US007674816B2

(12) United States Patent
Tao et al.

(10) Patent No.: US 7,674,816 B2
(45) Date of Patent: Mar. 9, 2010

(54) SUBSTITUTED MELATONIN DERIVATIVES, PROCESS FOR THEIR PREPARATION, AND METHODS OF USE

(75) Inventors: Chunlin Tao, Los Angeles, CA (US); Cheng-Zhi Yu, San Diego, CA (US); Neil P. Desai, Santa Monica, CA (US); Vuong Trieu, Calabasas, CA (US)

(73) Assignee: Abraxis BioScience, LLC, Los Angeles, CA (US)

( * ) Notice: Subject to any disclaimer, the term of this patent is extended or adjusted under 35 U.S.C. 154(b) by 0 days.

(21) Appl. No.: 10/583,804

(22) PCT Filed: Dec. 23, 2004

(86) PCT No.: PCT/US2004/043997

§ 371 (c)(1),
(2), (4) Date: Jan. 23, 2007

(87) PCT Pub. No.: WO2005/062992

PCT Pub. Date: Jul. 14, 2005

(65) Prior Publication Data

US 2007/0191463 A1   Aug. 16, 2007

Related U.S. Application Data

(60) Provisional application No. 60/531,955, filed on Dec. 23, 2003.

(51) Int. Cl.
*A61K 31/404* (2006.01)
*C07D 209/04* (2006.01)
(52) U.S. Cl. ...................... 514/415; 548/491
(58) Field of Classification Search ............. 548/491; 514/415
See application file for complete search history.

(56) References Cited

U.S. PATENT DOCUMENTS

| | | | |
|---|---|---|---|
| 4,087,444 A | 5/1978 | Flaugh et al. | |
| 4,614,807 A | 9/1986 | Flaugh | |
| 4,997,845 A | 3/1991 | Flaugh | |
| 5,196,435 A | 3/1993 | Clemens et al. | |
| 5,552,428 A | 9/1996 | Fraschini et al. | |
| 5,916,596 A | 6/1999 | Desai et al. | |
| 6,004,991 A * | 12/1999 | Fourtillan et al. | 514/415 |
| 6,180,657 B1 | 1/2001 | Flaugh | |
| 6,436,984 B1 | 8/2002 | Ducrocq et al. | |
| 6,506,405 B1 | 1/2003 | Desai et al. | |
| 6,537,579 B1 | 3/2003 | Desai et al. | |
| 6,552,064 B2 | 4/2003 | Attala | |
| 6,638,966 B2 | 10/2003 | Baker et al. | |

OTHER PUBLICATIONS

Chen, Jia Jun, Synthesis of 2-Iodo and 2-Phenyl-[11C]melatonin: Potential PET Tracers for Melatonin Binding Sites, Applied Radiation and Isotopes, 49(12) (1998), 1573-1579.*
Garratt, Peter J, Mapping the Melatonin Receptor. 3. Design and Synthesis of Melatonin Agonists and Antagonists Derived from 2-Phenyltryptamines, Journal of Medicinal Chemistry, 38(7) (1995), 1132-1139.*
Ito, Satoru, Acetone-Sensitized Photocoupling of 5-Bromouridine to Tryptophan Derivatives via Electron-Transfer Process, Journal of American Chemical Society, 102 (1980) 7535-754.*
Mor, Marco, Synthesis, Pharmacological Characterization and QSAR Studies on 2-Substituted Indole Melatonin Receptor Ligands, Bioorganic and Medicinal Chemistry, 9 (2001) 1045-1057.*
Rivara, Silvia, Three-Dimensional Quantitative Structure-Activity Relationship Studies on Selected MT1 and MT2 Melatonin Receptor Ligands: Requirements for Subtype Selectivity and Intrinsic Activity Modulation, Journal of Medicinal Chemistry, 46 (2003) 1429-1439.*
Sastre, J.A. Lopez, Biological activity of melatonin and some analogous: geometrical and electrical requirements, Journal of Molecular Structure (Thermochem) 53, (2001), 271-281.*
Spadoni, Gilberto, 2-Substituted 5-Methoxy-N-acyltryptamines: Synthesis, Binding Affinity for the Melatonin Receptor, and Evaluation of the Biological Activity, Journal of Medicinal Chemistry, 36, (1993), 4069-4074.*
Patani, George A. Bioisosterism: A rational approach in drug design. Chem. Rev. 96 (1996) 3147-3176.*
Clark et al., *Heterocycles*, 22 (1) 195-221 (1984).
Cole et al., *Life Sciences*, 35(17), 1755-1762 (1984).
Delagrange et al., *Clinical Neuropharmacology*, 20 (6) 482-510 (1997).
Duranti et al., *Life Sciences*, 51(7), 479-485 (1992).
Lawrence et al., *J. Neurochem.*, 45(3), 798-804(1985).
Li et al., *European J. Of Pharmacology*, 413, 63-72 (2001).
Mahle et al., *J. of Biological Rhythms*, 12 (6), 690-696 (Dec. 1997).
Mäkelä et al., *Molecular Pharmacology*, 52, 380-388 (1997).
Mathé-Allainmat et al., *Exp. Opin. Ther. Patents*, 7 (12), 1447-1458 (1997).
Marco et al., *Current Medicinal Chemistry*, 6, 501-518 (1999).
Naguib et al., *British J. Of Anesthesia*, 82 (6), 875-880 (1999).
Snieckus, *Chem. Rev.*, 90 (6), 879-933 (1990).
Sweetnam et al., *Molecular Pharmacology*, 29, 299-306 (1986).
Zarkovsky, *Neuropharmacology*, 26 (7A), 737-741 (1987).
International Search Report for PCT/USO4/43997 (Jun. 21, 2005).
Chemical Abstracts Service, Accession No. 1996:157889 (1996).
Chemical Abstracts Service, Accession No. 2003:749238 (2003).
Supplementary European Search Report for EP Application No. 04815983.4 (May 28, 2009).

* cited by examiner

*Primary Examiner*—Kamal A Saeed
*Assistant Examiner*—Samantha L Shterengarts
(74) *Attorney, Agent, or Firm*—Leydig, Voit & Mayer, Ltd.

(57) ABSTRACT

The invention provides 2 aryl substituted derivatives of melatonin. The invention further provides pharmaceutical compositions comprising such derivatives, methods for preparing such derivatives, and methods of using such derivatives to induce general anesthesia, sedation, and/or hypnotic or sleep effects in a patient, and to treat conditions affected by melatonin activity in a patient.

25 Claims, No Drawings

SUBSTITUTED MELATONIN DERIVATIVES, PROCESS FOR THEIR PREPARATION, AND METHODS OF USE

CROSS-REFERENCE TO RELATED PATENT APPLICATIONS

This patent application claims the benefit of U.S. Provisional Patent Application No. 60/531,955, filed on Dec. 23, 2003, which is incorporated by reference herein.

FIELD OF THE INVENTION

The present invention relates to derivatives of melatonin. More particularly, the invention provides aryl substituted melatonin derivatives, methods of preparation thereof, pharmaceutical compositions comprising aryl substituted melatonin derivatives, and methods of using same.

BACKGROUND OF THE INVENTION

Melatonin (N-acetyl-5-methoxytryptamine), formula (I),

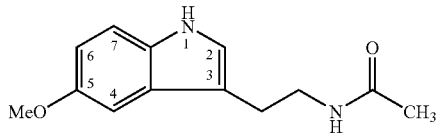

is a neurohormone produced primarily by the pineal gland, and to a lesser extent by extra pineal tissues such as the retina, harderian gland, and gastrointestinal tract. The synthesis of melatonin is regulated by circadian and seasonal variations in day length through a polysynaptic neuronal pathway from the retina to the pineal gland. Studies indicate that melatonin is involved in the transduction of photoperiodic information and appears to modulate a variety of neural and endocrine functions in vertebrates, including the regulation of reproduction, body weight, and metabolism in photopeliodic mammals, as well as the control of circadian rhythms and the modulation of retinal physiology. Melatonin has been detected in numerous central and peripheral tissues using the specific radioligand 2-[$^{125}$I]iodomelatonin described in Delagrange et al., *Clin. Neuropharinacol.*, 20, 482 (1997). Many of the effects of melatonin are mediated through high affinity G-protein-coupled receptors expressed primarily in the brain, retina, pituitary, and blood vessels (see, e.g., Mahle et al., *J. Biol. Rhymthms*, 12, 690 (1997)).

The search for novel high-affinity melatonin ligands has led to the synthesis of numerous indole and non-indole melatonin derivatives, and the elucidation of a structure-activity relationship for melatonin binding affinity (see, e.g., Methe-Allainmat et al., *Expert Opin. Ther. Pat.*, 7, 1447 (1997), and Mor et al., *Curr. Med. Chem.*, 6, 501-518(1999)). The melatonin derivatives were reported to be useful for treating desynchronization disorders (see, e.g., U.S. Pat. No. 6,180,657), and mammalian breast carcinoma in combination with antiestrogen compounds (see, e.g., U.S. Pat. No. 5,196,435). Melatonin derivatives also have been used as an antioxidant (see, e.g., U.S. Pat. No. 6,436,984), as well as a general anesthetic (see, e.g., U.S. Pat. No. 6,552,064). A general anesthetic is one which causes a patient to lose consciousness. This type of agent often is referred to as a "hypnotic" agent.

Low-level dosing of oral melatonin in a sublingual fashion has been shown to be effective for pre-medication prior to administering a general anesthetic (see, e.g., *British Journal of Anesthesia*, 82(6), 875-80 (1999)). In addition, U.S. Pat. No. 6,552,064 discloses the use of melatonin as a general anesthetic. Experiments disclosed therein demonstrate the effectiveness of melatonin for induction of general anesthesia in rats in comparison to other known anesthetics. Cumulative intravenous (iv) injection of divided doses of melatonin caused a progressive loss of righting reflex, grip strength, and eyelash reflex. The $ED_{95}$ (95% CI, for loss of righting reflex) of melatonin is 312 mg/mL, as compared to 8 mg/kg for thiopental, and 14.9 mg/kg for propofol. Bolus injection of 312 mg/mL of melatonin, or 10 mg/kg of propofol, caused an immediate loss of righting reflex.

There remains a need for new melatonin derivatives, and methods for using such derivatives to induce general anesthesia, hypnosis, or sleep in a subject. The invention provides such derivatives and methods. The inventive derivatives are more effective as an anesthetic than melatonin alone. Thus, the derivatives of the invention can be used in larger doses for general anesthesia, and in smaller doses for hypnosis, sedation, and sleep induction. These and other advantages of the invention, as well as additional inventive features, will be apparent from the description of the invention provided herein.

BRIEF SUMMARY OF THE INVENTION

In one aspect of the invention, there are provided melatonin derivatives, such as 2-aryl substituted melatonin. In another aspect of the invention, there is provided a method of preparing the above-described 2-aryl substituted derivatives of melatonin. In various embodiments, the invention provides a pharmaceutical composition comprising a melatonin derivative as described above and a pharmaceutically acceptable carrier. In another aspect of the invention, there is provided a method of using melatonin derivatives to induce general anesthesia, sedation, hypnosis, and/or sleep effects in a patient. The invention also provides a method of using melatonin derivatives to treat a condition affected by melatonin activity in a patient, such as depression, epilepsy, jet-lag, work-shift syndrome, sleep and chronobiological disorders, glaucoma, reproduction, cancer, premenstrual syndrome, immune disorders, inflammatory articular diseases, neurodegenerative diseases of the central nervous system (e.g., Parkinson's disease or Alzheimer's disease), neuroendocrine disorders, cholestatic oxidative stress, neuroprotection, sepsis and/or shock (e.g., induced by zymosan), myocardial dexorubicin toxicity, and for the treatment of carbon tetrachloride-induced acute liver injury. The melatonin derivatives of the present invention can also be used as an analgesic and as a combination analgesic and anesthetic.

The melatonin derivatives of the present invention can also be used as a broad spectrum antioxidant as a free radical scavenger, to reduce lipid peroxidation, for the treatment of spinal cord ischemia, as a prophylactic for reperfusion damage, such as ischemic reperfuision, to ameliorate oxidative organ damage, and in reducing lead-induced neurotoxicity. The melatonin derivatives described herein are also useful as a protectant against side effects induced by other active pharmaceutical agents, such as against gastric damage induced by omeprazole, against acetaminophen-induced side effects, against adriamycin-induced acute cardiac injury, in protecting against methotrixate hepatorenal oxidative innury, to treat chronic cyclosporin A nephrotoxicity, as a protectant against cyclophosphamide-induced myelosuppression, as a protectant against cisplatin-induced renal injury, as a protectant for lung toxicity induced by chlorpyrifos-ethyl, oxidative stress caused by delta-amino-evulinic acid, bleomycin-induced pulmonary fibrosis to attenuate acute renal failure and oxidative stress induced by mercuric chloride, as a protectant against cellular damage caused by ionizing radiation, as a protectant against gentamicin-induced nephrotoxicity.

DETAILED DESCRIPTION OF THE INVENTION

The aryl-substituted melatonin compounds in accordance with the present invention are represented by Formula II,

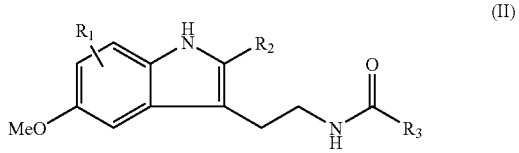

(II)

wherein, $R_1$ is hydrogen, halo, or nitro, $R_2$ is $C_4$-$C_{20}$ aryl, and $R_3$ is $C_1$-$C_{30}$ alkyl, $C_2$-$C_{22}$ alkenyl, $C_4$-$C_{20}$ aryl, $OR_4$, $SR_4$, $NR_4R_5$, $(CH_2)_nOR_4$, $(CH_2)_nSR_4$, $(CH_2)_nNR_4R_5$, $(CH_2)_nCOR_5$ wherein, n is 0-10;

$R_4$ and $R_5$, which can be the same or different, are hydrogen, $C_1$-$C_8$ alkyl, $C_1$-$C_6$ alkenyl and $C_4$-$C_{10}$ aryl.

An illustrative embodiment is the compound of Formula II wherein, $R_1$ is hydrogen, halo or nitro; $R_2$ is $C_4$-$C_{20}$ aryl; and $R_3$ is $C_1$-$C_6$ alkyl or $C_1$-$C_6$ alkoxy.

The following definitions are provided to better define the present invention. As used herein "halo" refers to fluoro, chloro, bromo, or iodo.

The term "alkyl" refers to an alkyl, substituted or unsubstituted, straight or branched chain alkyl or alkylenyl group, having from 1-30 carbon atoms. In view of availability of alkylating reactants, the alkyl group has preferably 1-22 carbon atoms. Illustrative of the alkyl group include the methyl, ethyl, propyl, isopropyl, cyclopropyl, butyl, isobutyl, sec-butyl, t-butyl, cyclobutyl, pentyl, 3-methylbutyl, 2,2-dimethylpropyl, 1,1-dimethylpropyl, hexyl, cyclohexyl, 1-methylpentyl, 4-methylpentyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, 1-pentylhexyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, 1-hexylnonyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl, docosinyl, tricosinyl, tetracosinyl and pentacosinyl groups.

The term "alkenyl" represents an alkenyl group, this has from 2 to 22 carbon atoms, and may be a straight or branched chain group, preferably, natural or unnatural fatty acid. It may have 1 or more, preferably from 2 to 6, double bonds. Examples of such groups include the vinyl, allyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 1-octenyl, 8-nonenyl, 1-nonenyl, 1-decenyl, 9-decenyl, 8-tridecenyl, cis-8-pentadecenyl, trans-8-pentadecenyl, 8-heptadecenyl, 8-heptadecenyl, 8,11-heptadecadienyl, 8,11,14-heptadecatrienyl, 4,7,11,14-nonadecatetraenyl and 2,6-dimethyl-8-(2,6,6-trimethyl-1-cyclohexen-1-yl)-1,3,5,7-nonatetraen-1-yl, cis-10-nonadecaenyl, 10,13-nonadecadienyl, cis-7,10,13-nonadecatrienyl, 5,8,11,14-nonadecatetraenyl, nonadecapentaenyl, henecosatetraenyl, henecosapentaenyl, henecosahexaenyl.

The term "alkoxy" refers to an alkoxy group, and may be a straight or branched chain group, substituted or unsubstituted with 1 to 20 carbon. Examples of such groups include the methoxy, ethoxy, propoxy, isopropoxy, butoxy, isobutoxy, sec-butoxy, t-butoxy, pentoxy, 3-methylbutoxy, 2,2-dimethylpropoxy, 1,1-dimethylpropoxy, hexyloxy, cyclohexyloxy, phenyloxy, 1-methylpentyloxy, 4-methylpentyloxy, heptyloxy, 1-methylhexyloxy, 2-methylhexyloxy, 5-methylhexyloxy, 3-ethylpentyloxy, octyloxy, 2-methylheptyloxy, 6-methylheptyloxy, 2-ethylhexyloxy, 2-ethyl-3-methylpentyloxy, 3-ethyl-2-methylpentyloxy, nonyloxy, 2-methyloctyloxy, 7-methyloctyloxy, 4-ethylheptyloxy, 3-ethyl-2-methylhexyloxy, 2-ethyl-1-methylhexyloxy, decyloxy, 2-methylnonyloxy, 8-methylnonyloxy, 5-ethyloctyloxy, 3-ethyl-2-methylheptyloxy, 3,3-diethylhexyloxy, undecyloxy, 2-methyldecyloxy, 9-methyldecyloxy, 4-ethylnonyloxy, 3,5-dimethylnonyloxy, 3-propyloctyloxy, 5-ethyl-4-methyloctyloxy, 1-pentylhexyloxy, dodecyloxy, 1-methylundecyloxy, 10-methylundecyloxy, 3-ethyldecyloxy, 5-propylnonyloxy, 3,5-diethyloctyloxy, tridecyloxy, 11-methyldodecyloxy, 7-ethylundecyloxy, 4-propyldecyloxy, 5-ethyl-3-methyldecyloxy, 3-pentyloctyloxy, tetradecyloxy, 12-methyltridecyloxy, 8-ethyldodecyloxy, 6-propylundecyloxy, 4-butyldecyloxy, 2-pentylnonyloxy, pentadecyloxy, 13-methyltetradecyloxy, 10-ethyltridecyloxy, 7-propyldodecyloxy, 5-ethyl-3-methyldodecyloxy, 4-pentyldecyloxy, 1-hexylnonyloxy, hexadecyloxy, 14-methylpentadecyloxy, 6-ethyltetradecyloxy, 4-propyltridecyloxy, 2-butyldodecyloxy, heptadecyloxy, 15-methylhexadecyloxy, 7-ethylpentadecyloxy, 3-propyltetradecyloxy, 5-pentyldodecyloxy, octadecyloxy, 16-methylheptadecyloxy, 5-propylpentadecyloxy, nonadecyloxy, 17-methyloctadecyloxy, 4-ethylheptadecyloxy, icosyloxy and 18-methylnonadecyloxy, 3-ethyloctadecyloxy groups.

The term "aryl" refers to an aromatic or heteroaromatic ring, including by way of example, phenyl, naphthyl furanyl, thionyl rings with 4 to 20 carbons. The aryl ring can be substituted or unsubstituted. Substituents include halo, $C_1$-$C_6$ alkyl, which by way of example can be substituted, for example, by halogen, $C_1$-$C_6$ alkoxy, amino, alkylamino, thiol, alkylthiol, hydroxyl, —CHO, —$NO_2$, phenyl, vinyl, —CN, $Si(CH_3)_3$, —$OCH_2O$—, and combinations thereof. The aryl ring can be substituted with any of one, two, three, four or five, or more substituents, depending on the size of the ring. Examples of $C_4$-$C_{20}$ aryl groups include phenyl, 4-(fluorophenyl), 3-(fluorophenyl), 2-(fluorophenyl), 4-(chlorophenyl), 3-(chlorophenyl), 2-(chlorophenyl), 4-(methylphenyl), 3-(methylphenyl), 2-(methylphenyl), 4-(methoxyphenyl), 3-(methoxyphenyl), 2-(methoxyphenyl), 4-(ethoxyphenyl), 3-(ethoxyphenyl), 2-(ethoxyphenyl), 4-(vinylphenyl), 4-(acetylphenyl), 3-(acetylphenyl), 2-(acetylphenyl), 4-(trifluoromethylphenyl), 3-(trifluoromethylphenyl), 4-(trimethylsilylphenyl), 3-(trimethylsilylphenyl), 4-(methylthiophenyl), 4-(tert-butylphenyl), 4-(dimethylaminophenyl), 4-(ethylphenyl), 4-(benzoxyphenyl), 4-(biphenyl), 2-furanyl, 2-(thiophenyl), 2-(5-methylthiophenyl), 3-(thiophenyl), 2-(indolyl), 1-(naphthalenyl), 2-(naphthalenyl), 4-(dibenzofuranyl), 1-(thianthrenyl), 2,3-(dichlorophenyl), 2,5-(dichlorophenyl), 3,4-(dichlorophenyl), 3,5-(dichlorophenyl), 2,3-(difluorophenyl), 2,4-(difluorophenyl), 2,5-(difluorophenyl), 2,6-(difluorophenyl), 3,4-(difluorophenyl), 3,5-difluorophenyl), 3,5-(dibromophenyl), 3,5-(bis(trifluoromethyl)phenyl), 2,3-(dimethylphenyl), 2,5-(dimethylphenyl), 2,6-(dimethylphenyl), 3,5-(dimethylphenyl), 2,4-(dimethoxyphenyl), 2,5-(dimethoxyphenyl), 3,4-(dimethoxyphenyl), 2,3,4-(trimethoxyphenyl), 2,4,6-(trifluorophenyl), 2,3,4,5,6-(pentafluorophenyl), and the like.

While all of the compounds of Formula II are believed to be useful as a general anesthetic, certain of such compounds are preferred for such use. Preferred compounds of Formula II for use in the invention include those compounds wherein $R_1$ is hydrogen, $R_2$ is a substituted phenyl (preferably 4-substituted phenyl), and $R_3$ is $C_1$-$C_4$ alkyl (preferably methyl or ethyl).

The following structures are preferred embodiments of the invention:

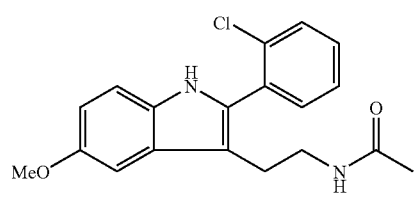

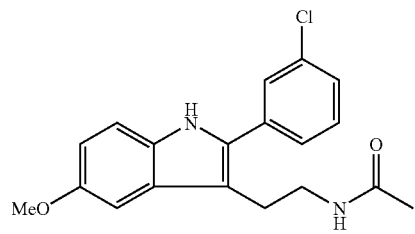

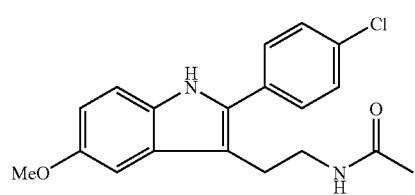

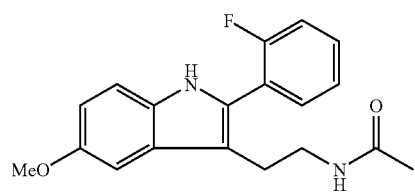

-continued

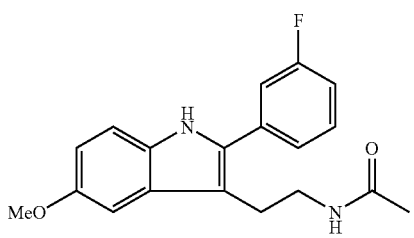

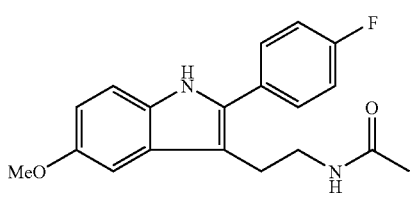

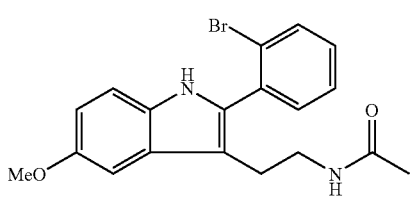

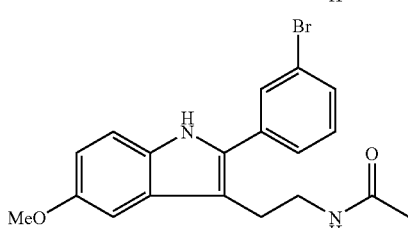

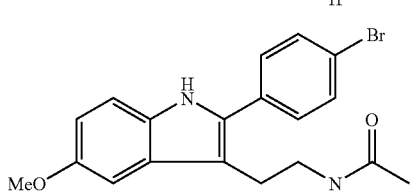

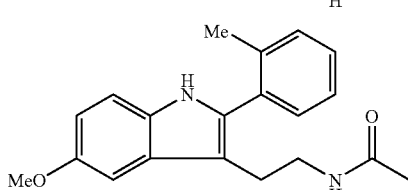

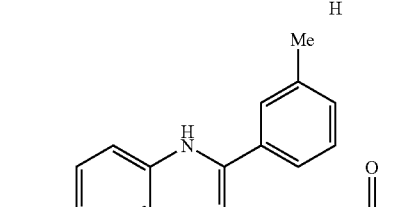

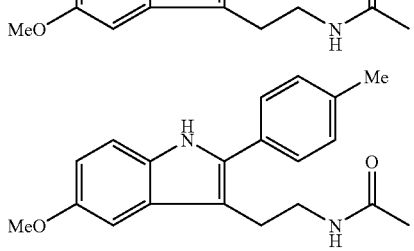

-continued
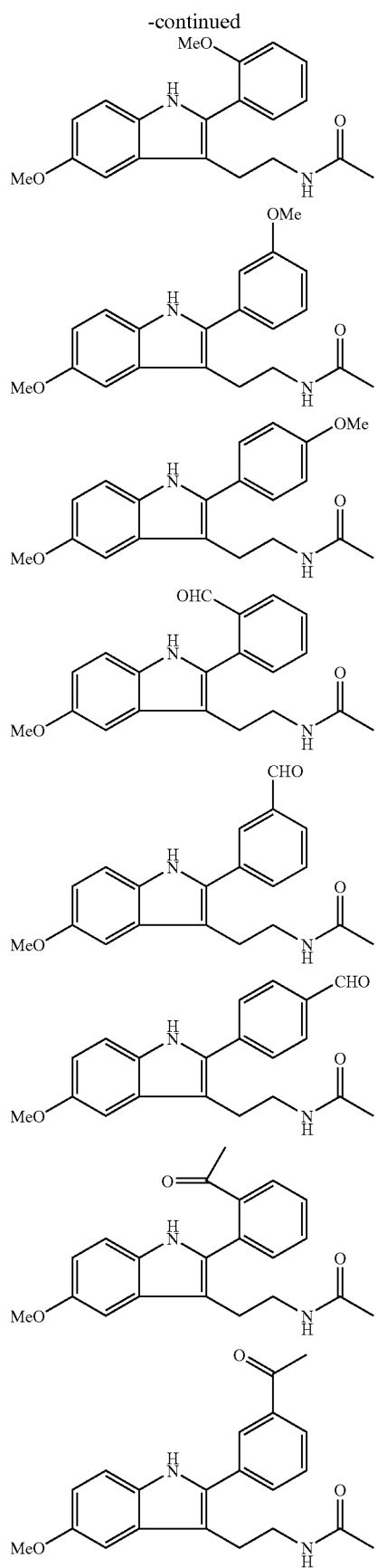
-continued
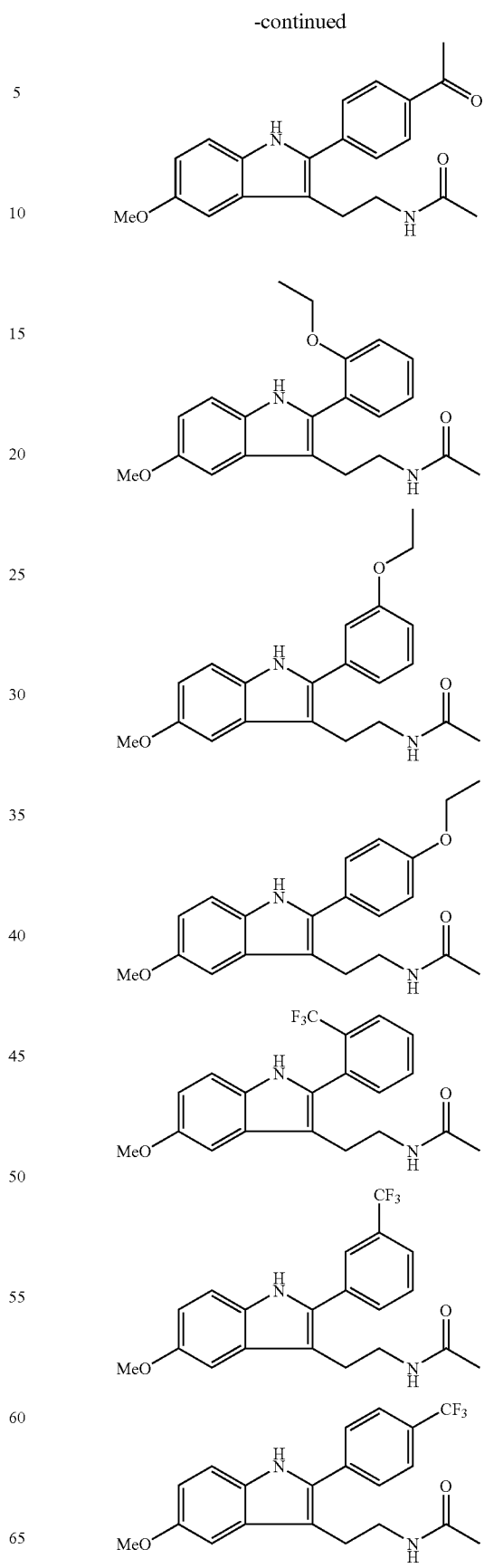

-continued
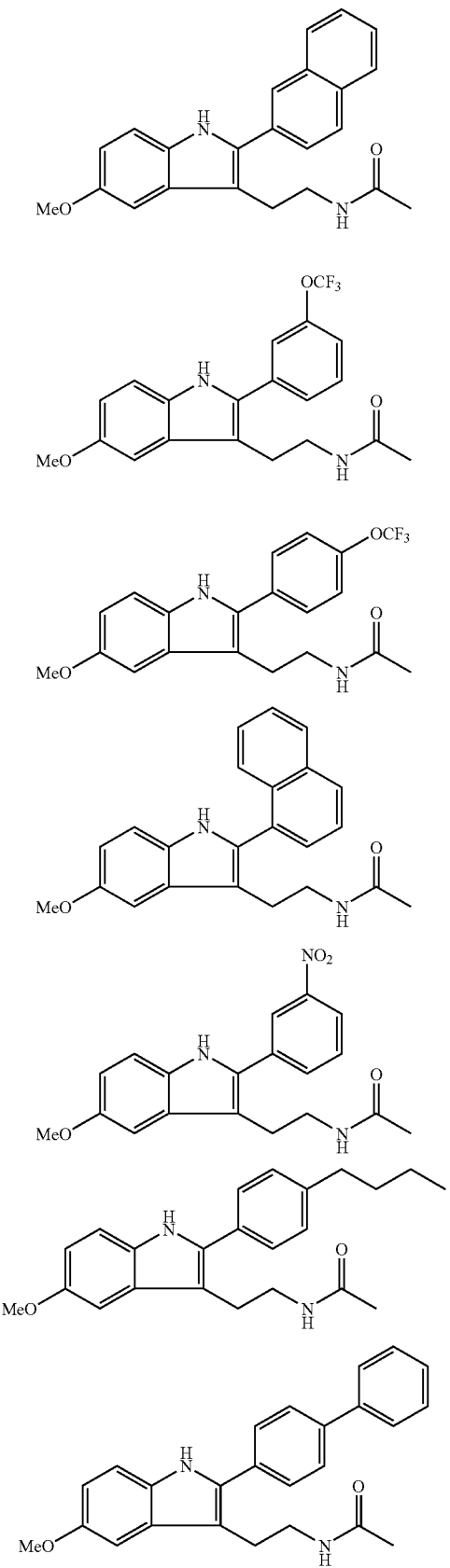
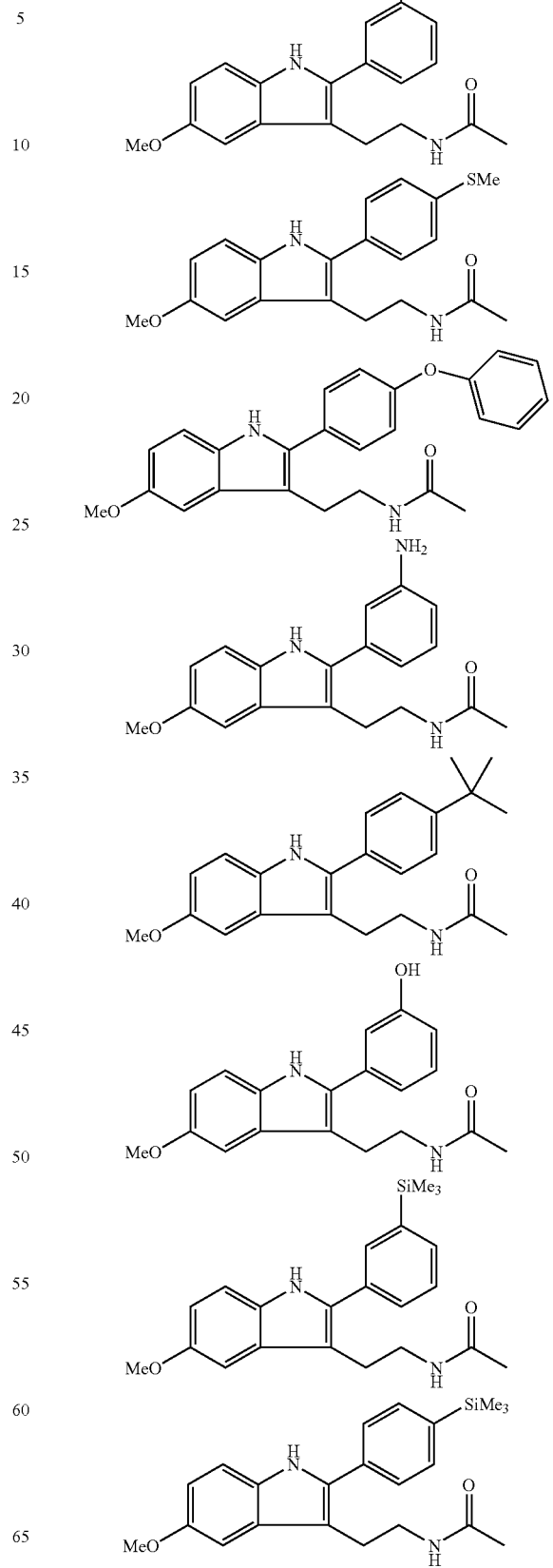

-continued
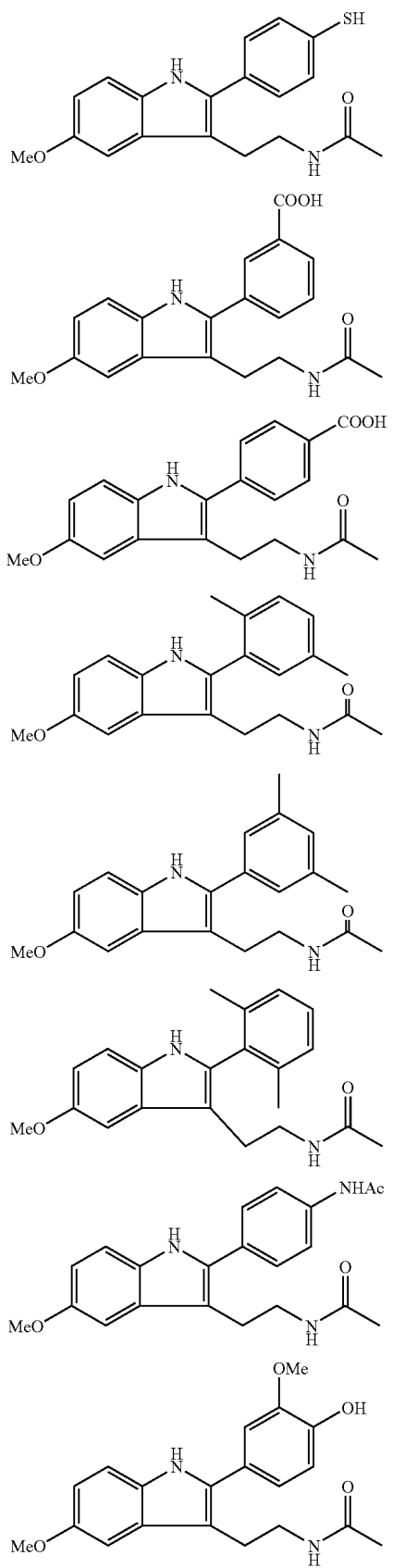
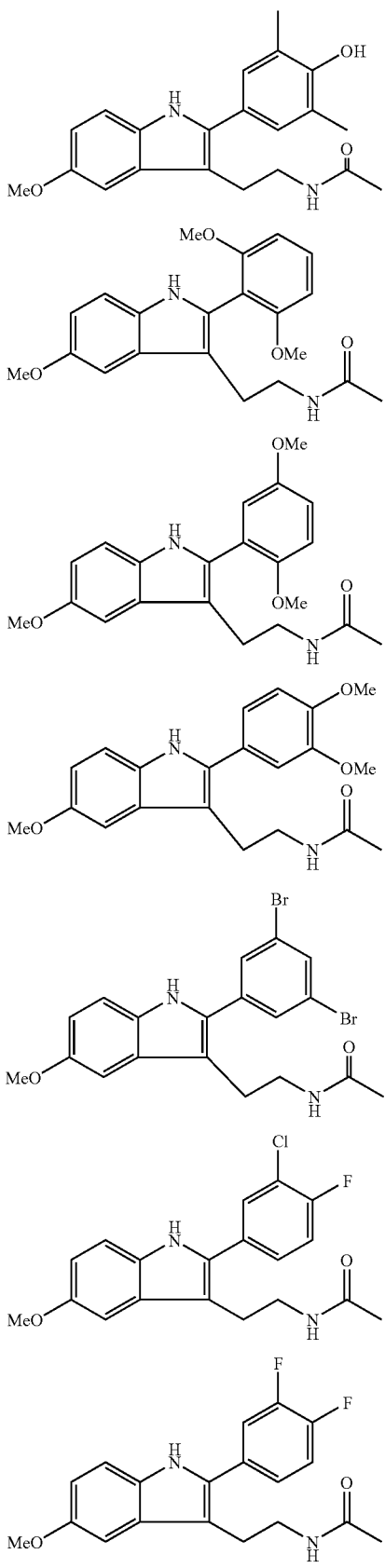

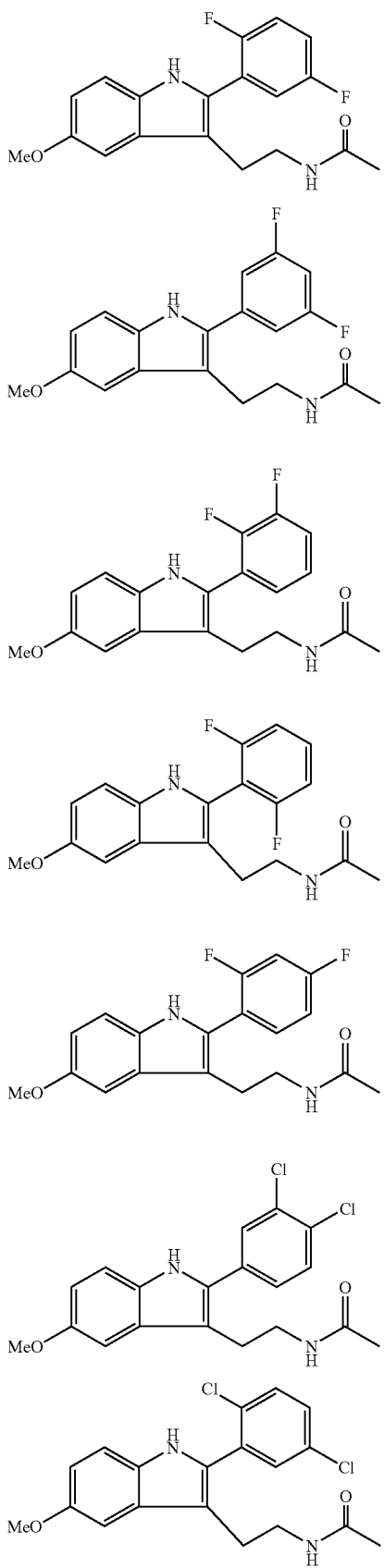
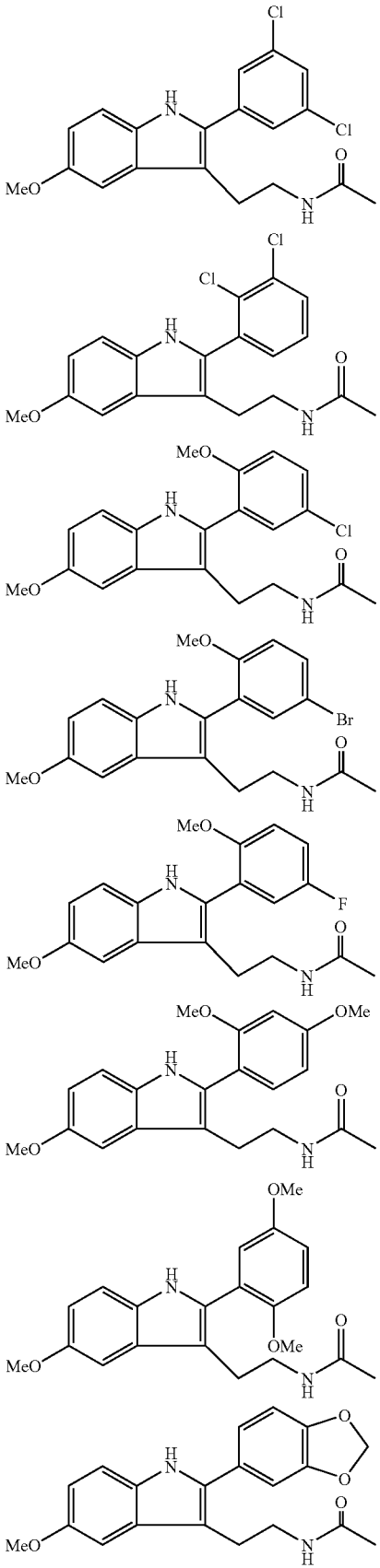

-continued
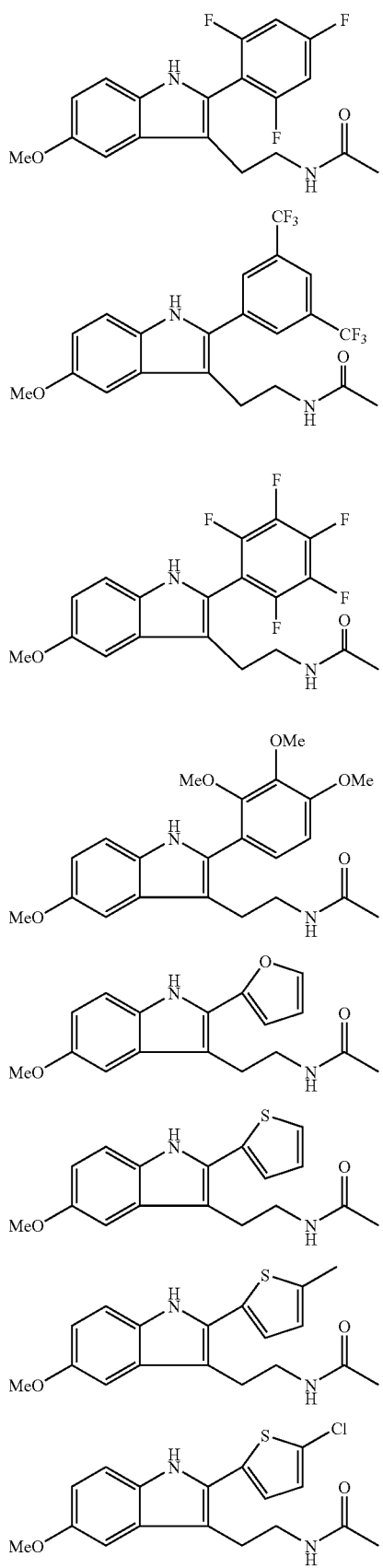
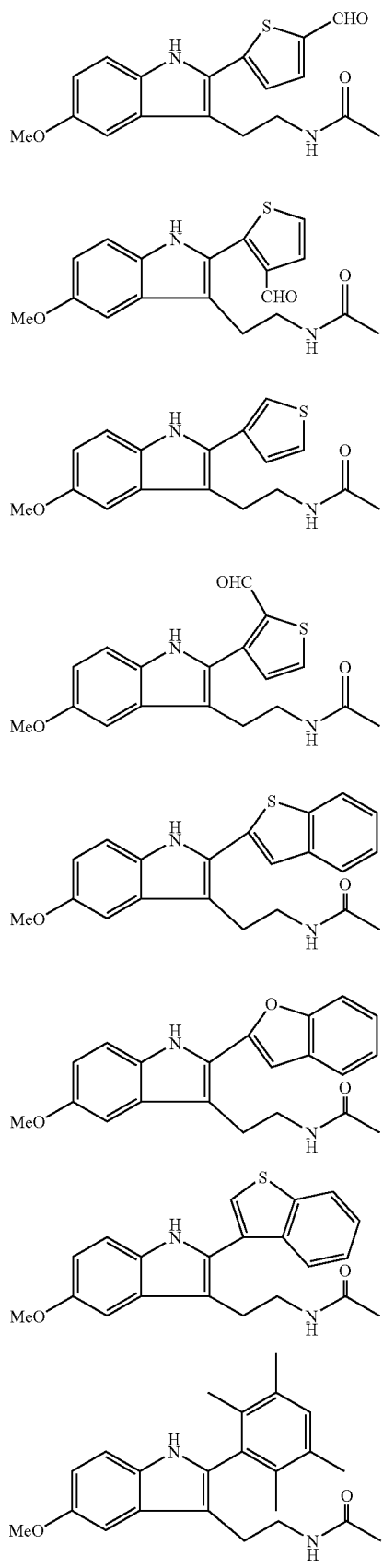

-continued

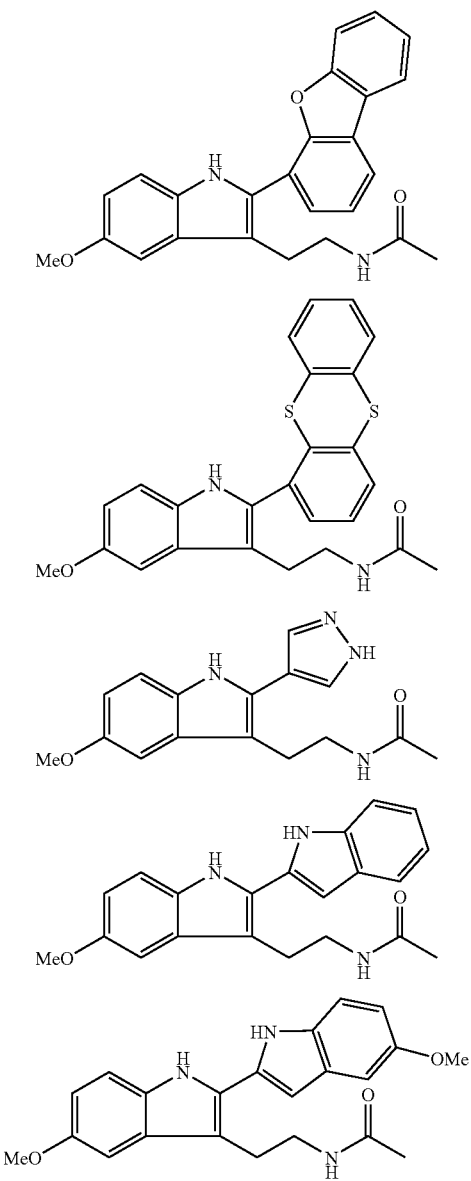

Compounds of formula II are preferably prepared by reacting a 2-halo melatonin with aryl boronic acid in the presence of a metal catalyst (e.g., a palladium catalyst) as set forth, for example, in Scheme 1.

Scheme 1

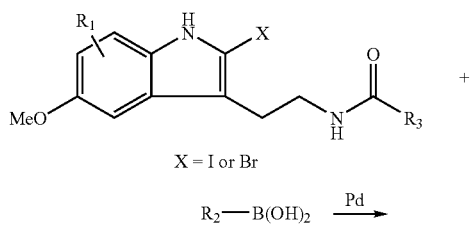

-continued

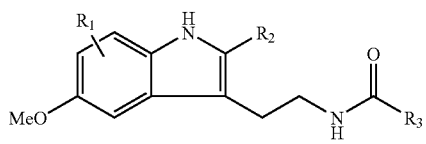

Generally, any 2-halo melatonin analog and any aryl boronic acid can be used for the preparation of the compounds of the invention. Aryl boronic acid is commercially available or it can be prepared according to procedures known in the art. For example, the aryl boronic acid can be prepared from an aryl halide such as is described in, for example, Snieckus, Chem. Rev., 90, 879 (1990). The 2-bromomelatonin or 2-iodomelatonin starting material can be prepared according to procedures known in the art (see, e.g., U.S. Pat. No. 5,552,428 and Duranti et al., Life Sci., 51, 479 (1992)). In a particularly preferred embodiment of the invention, 2-halomelatonin and aryl boronic acid, preferably in the equivalent mole ratio, are heated in the presence of palladium catalyst under argon or nitrogen to about 50-120° C. for 5-10 hours with a mechanical stirrer. The palladium catalyst is removed by filtration and the filtrate is concentrated and purified by column chromatography with ethyl acetate-hexanes (10-50%) as an eluant. The pure product obtained typically is a white or yellow powder. The reaction yields range from 20% to 90%.

Other starting materials that can be employed in the preparation of the 2-aryl melatonin derivatives of the present invention are known and can be made by methods known in the art (see, e.g., U.S. Pat. Nos. 4,087,444, 4,614,807, and 4,997,845). Methods for the preparation of various indole derivatives are disclosed in, for example, Heterocycles, 22(1), 195 (1984).

The binding profile of exemplary inventive compounds to neurotransmitter receptor sites is set forth below in Table 1. The characterization of the receptors, isolation of the membrane, and enzyme assay have been described in detail previously (see, e.g., Cole et al., Life Sci., 35, 1755 (1984), Lawrence et al., J. Neurochem., 45(3), 798 (1985), Sweetnam et al., Mol. Pharmacology, 29, 299 (1986), Zarkovsky et al., Neuropharmacology, 26 (7A), 737 (1987), Li et al., Eur. J. Pharmacology, 413, 63 (2001), and Markela et al., Mol. Pharmacology, 52, 380 (1997)).

The melatonin binding site on $GABA_A$ was defined using a series of competitive binding assays. Frozen bovine hippocampus was thawed and homogenized in 40 volumes of ice-cold 0.32 M sucrose. The suspension was centrifuged at 1000×g for 10 minutes at 4° C. The pellet was washed twice in assay buffer and reacted with radioactive ligand in presence or absence of melatonin at $10^{-4}$ M final concentration. The amount of radioactivity remained on the Whatman filter following filtration of the reaction mix and two washes with assay buffer was determined using a liquid scintillation counter. Inhibition of radioactive ligand binding by melatonin represents the competitive binding of melatonin to the same site as the radioactive ligand. $GABA_A$ agonist site, $GABA_A$ α-1 site, $GABA_A$ α-5 site, $GABA_A$ α-6 site, and $GABA_A$ Cl channel were assayed using $^3$H-GABA, $^3$H-flunitrazepam, $^3$H-RY80, $^3$H-Ro 15-4513, and $^3$H-TBOB.

TABLE 1

Specific binding of melatonin to the $GABA_A$ receptors.

| Chemical | Conc. (M) | Neurotransmitter Related, $GABA_A$ | | | | |
|---|---|---|---|---|---|---|
| | | Agonist site | Alpha 1 site | Alpha 5 site | Alpha 6 site | Ion Channels $Cl^-$, TBOB site |
| Melatonin | 1.0E−3 | −3.11% | 39.80% | 15.19% | 17.50% | 39.44% |
| 6-Chloromelatonin | 1.0E−3 | −13.74% | 12.49% | 13.95% | −7.74% | 43.63% |
| 2-Bromomelatonin | 1.0E−3 | −8.55% | 8.35% | −2.02% | −12.69% | 51.87% |
| 2-Phenylmelatonin | 1.0E−4 | 0.33% | 35.16% | 17.92% | 12.48% | 84.28% |
| Luzindole | 1.0E−4 | 5.84% | 5.09% | −1.37% | 4.93% | 47.55% |
| 2-(4-Fluorophenyl) melatonin | 1.0E−4 | nd | 28.80% | 20.59% | 20.76% | 110.10% |
| 2-(4-Trifluoromethylphenyl) melatonin | 1.0E−4 | nd | 8.11% | 17.87% | 25.87% | 103.23% |
| 2-(4-Methylphenyl) melatonin | 1.0E−4 | nd | 10.28% | 22.26% | 32.93% | 101.46% |
| 2-(3-Trifluoromethylphenyl) melatonin | 1.0E−4 | nd | 15.61% | 29.31% | 25.39% | 79.60% |
| 2-(4-Methoxyphenyl) melatonin | 1.0E−4 | nd | −8.16% | 7.09% | 6.68% | 108.82% |
| 2-(4-t-Butoxyphenyl) melatonin | 1.0E−4 | nd | −13.46% | 6.04% | 19.60% | 91.94% |
| 2,6-Diisopropylphenol | 1.0E−4 | 12.48% | −14.31% | −15.58% | −0.89% | 117.52% | nd: not determined

The compounds of the invention can be formulated into compositions comprising pharmaceutically acceptable carriers for administration to a patient (e.g., a human patient). Any number of suitable pharmaceutically acceptable carriers can be used as a vehicle for the administration of the inventive compounds. Preferably, the inventive compounds are formulated for general pharmaceutical use. Most preferably, the inventive compounds are formulated for use as an anesthetic.

The composition can be administered to a patient (e.g., a human patient) according to conventional methods for anesthesia. Such methods include, for example, oral administration, nasal administration, bolus injection, intravenous administration by repeated doses or by continuous infusion, rectal administration, vaginal administration, sublingual administration, cutaneous administration, and by slow release routes. Preferably, the pharmaceutical composition is administered by continuous infusion. In some embodiments, the pharmaceutical composition can be administered by two or more routes, such as by bolus injection followed by continuous intravenous administration.

Typically, the composition is mixed with, diluted by, or enclosed within a carrier which can be in the form of a capsule, sachet, paper, or other container. When the carrier serves as a diluent, it can be a solid, semi-solid, or liquid material which acts as a vehicle, excipient, or medium for the active ingredient. Thus, the inventive composition can be in the form of tablets, pills, powders, lozenges, sachets, cachets, elixirs, suspensions, emulsions, solutions, syrups, aerosols (as a solid or in a liquid medium), ointments which contain, for example, up to 10% by weight of the active compound, soft and hard gelatin capsules, suppositories, sterile injectable solutions, and sterile packaged powders.

For oral administration, the 2-aryl substituted melatonin derivatives are incorporated into suitably flavored syrups, aqueous or oil suspensions, and flavored emulsions with edible oils such as cottonseed oil, sesame oil, coconut oil, or peanut oil, as well as elixirs and similar pharmaceutical vehicles. Suitable dispersing or suspending agents for aqueous suspensions include, for example, synthetic and natural gums such as tragacanth, acacia, alginate, dextran, sodium carboxymethylcellulose, methylcellulose, polyvinylpyrrolidone, or gelatin.

Pharmaceutical compositions for inhalation or insufflation include solutions and suspensions in pharmaceutically acceptable, aqueous or organic solvents, or mixtures thereof, and powders. The liquid compositions can contain suitable pharmaceutically acceptable excipients as set forth above. Preferably the inventive composition is administered orally or nasally for local or systemic effect. Compositions formulated in sterile pharmaceutically acceptable solvents can be nebulised by use of inert gases. Nebulised solutions can be breathed directly from the nebulising device, or the nebulising device can be attached to a face mask, tent, or intermittent positive pressure breathing machine. Compositions in solution, suspension, nanoparticle, or powder can be administered, preferably orally or nasally, from devices which deliver the formulation in an appropriate manner.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents or flavoring agents. The compositions can be formulated so as to provide rapid, sustained or delayed release of the active ingredient after administration to the patient by employing procedures well known in the art.

Preferred compositions for administration by injection include those comprising a biologically active melatonin derivative and a surface-active agent (or wetting agent or surfactant) or a derivative in the form of an emulsion (e.g., a water-in-oil or oil-in-water emulsion). Suitable surface-active agents include, but are not limited to, nonionic agents, such as polyoxyethylenesorbitans (e.g., Tween™ 20, 40, 60, 80, or 85) and other sorbitans (e.g., Span™ 20, 40, 60, 80, or 85). Other ingredients such as mannitol or other pharmaceutically acceptable vehicles can be added.

The invention also provides compositions and methods useful for in vivo delivery, as well as compositions comprising nanoparticles of the inventive composition that are suitable for parenteral administration in aqueous suspension.

It is well known that colloidal nanoparticles or particles less than 200 nanometers (nm) in size have been widely used in various formulations. The preparation of nanoparticles from biocompatible polymers (e.g., albumin) is disclosed in, for example, U.S. Pat. Nos. 5,916,596, 6,506,405, and 6,537,579. A large number of conventional pharmacologically active agents circulate in the blood stream bound to carrier proteins (through hydrophobic or ionic interactions), such as, for example, human serum albumin. Thus, compositions comprising the inventive compound and one or more proteins (e.g., human serum albumin) are believed to provide for a pharmacologically active agent that is "pre-bound" to a protein (through hydrophobic or ionic interactions) prior to administration.

In accordance with the invention, nanoparticles of the inventive compound are prepared using a solvent evaporation technique from an oil-in-water emulsion prepared under conditions of high shear forces (e.g., sonication, high pressure homogenization, or the like).

The invention also provides submicron particles in powder form, which can easily be reconstituted in water or saline. The powder is obtained after removal of water by lyophilization. Preferably, human serum albumin serves as the structural component of the nanoparticles of the inventive compound, as well as a cryoprotectant and reconstitution aid. The preparation of particles filterable through a 0.22 micron filter according to the method as described herein, followed by drying or lyophilization, produces a sterile solid formulation useful for intravenous injection.

Several biocompatible materials can be employed in the practice of the present invention for the formation of a polymeric shell. Suitable biocompatible materials include, for example, naturally occurring materials such as proteins, polypeptides, oligopeptides, polynucleotides, polysaccharides (e.g., starch, cellulose, dextrans, alginates, chitosan, pectin, hyaluronic acid, and the like), and lipids. Examples of suitable proteins that can be used in the invention include albumin, insulin, hemoglobin, lysozyme, immunoglobulins, α-2-macroglobulin, fibronectin, vitronectin, fibrinogen, casein, and the like, as well as combinations of any two or more thereof. Alternatively, the biocompatible material can be prepared using synthetic polymers. Examples of suitable synthetic polymers include polyalkylene glycols (e.g., linear or branched chain), polyvinyl alcohol, polyacrylates, polyhydroxyethyl methacrylate, polyacrylic acid, polyethyloxazoline, polyacrylamides, polyisopropyl acrylamides, polyvinyl pyrrolidinone, polylactide/glycolide and the like, and combinations thereof.

The inventive pharmaceutical composition can optionally employ a dispersing agent to suspend or dissolve the inventive compound. Preferred dispersing agents include, for example, volatile liquids such as dichloromethane, chloroform, ethyl acetate, benzene, and the like (e.g., solvents that have a high degree of solubility for the pharmacologically active agent, and are soluble in the other dispersing agent employed), in combination with a less volatile dispersing agent. The addition of volatile additives enhances the solubility of the pharmacologically active agent into the dispersing agent. Following dissolution, the volatile component can be removed by evaporation (e.g., under vacuum).

The inventive pharmaceutical composition can be used for general anesthesia to facilitate surgery, drug or alcohol withdrawal, treatment of tetanus, and other diagnostic or therapeutic interventions. In particular, the present invention can be used to maintain general anesthesia for extended periods (e.g., 24-48 hours) in addicted patients during drug and/or alcohol withdrawal. The invention can be used to maintain general anesthesia for prolonged periods (e.g., days to weeks) in the management of patients with tetanus. The inventive pharmaceutical composition can be used as an oral sedative or sleeping pill (e.g. AMBIEN®). The inventive pharmaceutical composition can also be used to render patients sedated and pain-free to facilitate surgical and other therapeutic interventions (e.g., endotracheal mechanical ventilation and wound dressing change in patients with burns), or diagnostic procedures (e.g., endoscopy and imaging techniques) for which loss of consciousness is not required (i.e., "conscious sedation").

The invention further provides a method for treating a condition affected by melatonin activity in a patient. The method comprises administering to the patient a therapeutically effective amount of the inventive pharmaceutical composition; Any condition affected by melatonin activity can be treated by the inventive method. Examples of such conditions include, for example, depression, epilepsy, work-shift syndrome, sleep and chronobiological disorders, glaucoma, reproduction, premenstrual syndrome, immune disorders, inflammatory articular diseases, neuroendocrine disorders, sleep disorders associated with jet lag, neurodegenerative diseases of the central nervous system (e.g., Parkinson's disease or Alzheimer's disease), and certain types of cancer. The inventive pharmaceutical composition also can be used as a contraceptive or as an analgesic (e.g. aspirin) to relieve pain by raising the pain threshold without a loss of consciousness.

The following examples further illustrate the invention but, should not be construed as in any way limiting in its scope.

Example 1

This example illustrates the preparation of N-(2-(2-bromo-5-methoxy-1H-indol-3-yl)ethyl)acetamide. Melatonin (2.0 g, 8.61 mmol) was dissolved in a mixture of THF (40 mL) and $CHCl_3$ (40 mL). Pyridinium tribromide (3.5 g, 10.3 mmol) was added, and the mixture was stirred for 35 minutes at 0° C. Aqueous NaOH (2 N) was added to quench the reaction and adjust the solution to pH 13. The mixture was extracted with ethyl acetate (200 mL), and the organic layer was washed with brine, dried over anhydrous sodium sulfate, and filtered. After condensation, the crude product was purified by flash column chromatography (hexanes: ethyl acetate, 1:1) and a colorless solid (1.9 g, 6.13 mmol, 71%) was obtained. $^1$H NMR($CDCl_3$, 400 MHz): 8.19 (brs, 1H), 7.20 (dd, J=8.8, 2.9 Hz, 1H), 6.97 (d, J=2.4 Hz, 1H), 6.84 (dd, J=8.9, 2.4 Hz, 1H), 5.66 (brs, 1H), 3.85 (s, 3H), 3.53 (dd, J=13.5, 6.4 Hz, 2H), 2.92 (t, J=6.6 Hz, 2H), 1.94 (s, 3H). ESI-MS: calcd. for $C_{13}H_{16}BrN_2O_2$ (MH$^+$) 311, found 311.

Example 2

This example illustrates the preparation of N-(2-(2-(4-fluorophenyl)-5-methoxy-1H-indol-3-yl)ethyl)acetamide. N-(2-(2-bromo-5-methoxy-1H-indol-3-yl)ethyl)acetamide (275 mg, 0.89 mmol) was dissolved in a mixture of toluene (11 mL) and ethanol (11 mL). 4-fluorophenylboronic acid (186 mg, 1.33 mmol), LiCl (113 mg, 2.66 mmol) and aqueous sodium carbonate (2.2 mL, 1M) were sequentially added to the solution. Palladium (5 mg) was then added in the presence of an argon atmosphere. The mixture was refluxed for 4 hours, and the crude product was purified via flash column chromatography (hexanes:ethyl acetate, 1:1). The final product was a yellow solid (221 mg, 76%). $^1$H NMR (CDCl$_3$, 500 MHz): 8.08 (brs, 1H), 7.52 (dd, J=8.8, 5.4 Hz, 2H), 7.29-7.16 (m, 4H), 6.88 (dd, J=8.6, 2.3 Hz, 1H), 3.88 (s, 3H), 3.51 (dd, J=12.8, 6.9 Hz, 2H), 3.05 (t, J=7.0 Hz, 2H), 1.82 (s, 3H). ESI-MS: calcd. for C$_{19}$H$_{19}$FN$_2$O$_2$Na (M+Na$^+$) 349, found 349.

Example 3

This example illustrates the preparation of N-(2-(5-methoxy-2-phenyl-1H-indol-3-yl)ethyl)acetamide. N-(2-(2-bromo-5-methoxy-1H-indol-3-yl)ethyl)acetamide (248 mg, 0.8 mmol) was dissolved in a mixture of toluene (9.5 mL) and ethanol (9.5 mL). Phenylboronic acid (145 mg, 1.19 mmol), LiCl (102 mg, 2.41 mmol), and aqueous sodium carbonate (2 mL, 1M) were sequentially added to the solution. Palladium was then added to the mixture in the presence of an argon atmosphere. The mixture was refluxed for 5 hours, and the crude product was purified via flash column chromatography (hexanes:ethyl acetate, 1:1). The final product was yellow solid (130 mg, 53%). $^1$H NMR (CDCl$_3$, 500 MHz): 8.00 (brs, 1H), 7.56 (dd, J=7.9 Hz, 2H), 7.48 (t, J=7.5 Hz, 2H), 7.38 (t, J=7.4 Hz, 1H), 7.29 (d, J=8.7 HZ, 1H), 7.10 (d, J=2.3 Hz, 1H), 6.89 (dd, J=8.8, 2.4 Hz, 1H), 5.46 (brs, 1H), 3.89 (s, 3H), 3.55 (dd, J=12.5, 6.4 Hz, 2H), 3.11 (t, J=6.7 Hz, 2H), 1.78 (s, 3H). ESI-MS: calcd. for C$_{19}$H$_{21}$N$_2$O$_2$(MH$^+$) 309, found 309.

Example 4

This example illustrates the preparation of N-(2-(5-methoxy-2-methoxyphenyl-1H-indol-3-yl)ethyl)acetamide. N-(2-(2-bromo-5-methoxy-1H-indol-3-yl)ethyl)acetamide (286 mg, 0.92 mmol) was dissolved in a mixture of toluene (11 mL) and ethanol (11 mL). 4-methoxyphenylboronic acid (210 mg, 1.38 mmol), LiCl (117 mg, 2.76 mmol), and aqueous sodium carbonate (2.3 mL, 1M) were sequentially added to the solution. Palladium was then added to the mixture in the presence of an argon atmosphere. The mixture was refluxed for 3 hours, and the crude product was purified by flash column chromatography (hexanes:ethyl acetate, 2:3). The final product was a yellow solid (280 mg, 90%). $^1$H NMR (CDCl$_3$, 500 MHz): 8.01 (brs, 1H), 7.50-7.42 (m, 3H), 7.07-6.87 (m, 3H), 6.86 (dd, J=8.7, 2.4 Hz, 1H), 5.49 (brs, 1H), 3.88 (s, 3H), 3.86 (s, 3H), 3.53 (dd, J=13.0, 6.8 Hz, 2H), 3.06 (t, J=6.9 Hz, 2H), 1.80 (s, 3H). ESI-MS: calcd. for C$_{20}$H$_{22}$N$_2$O$_3$Na (M+Na$^+$) 361, found 361.

Example 5

This example illustrates the preparation of N-(2-(5-methoxy-2-p-tolyl-1H-indol-3-yl)ethyl)acetamide. N-(2-(2-bromo-5-methoxy-1H-indol-3-yl)ethyl)acetamide (258 mg, 0.83 mmol) was dissolved in a mixture of toluene (10 mL) and ethanol (10 mL). 4-methylphenylboronic acid (169 mg, 1.24 mmol), LiCl (106 mg, 2.49 mmol) and aqueous sodium carbonate (2.1 mL, 1M) were sequentially added to the solution. Palladium (5 mg) was then added in the presence of an argon atmosphere. The mixture was refluxed for 4.5 hours, and the crude product was purified on flash column chromatography (hexanes:ethyl acetate, 1:2). The final product was a yellow foam (221 mg, 83%). $^1$H NMR (CDCl$_3$, 500 MHz): 7.99 (s, 1H), 7.47-7.44 (m, 2H), 7.29-7.26 (m, 3H), 7.08 (d, J=2.4 Hz, 1H), 6.87 (dd, J=8.8, 2.4 Hz, 1H), 5.45 (brs, 1H), 3.88 (s, 3H), 3.54 (dd, J=12.7, 6.8 Hz, 2H), 3.09 (t, J=6.8 Hz, 2H), 2.41 (s, 3H), 1.78 (s, 3H). ESI-MS: calcd. for C$_{20}$H$_{22}$N$_2$O$_2$Na (M+Na$^+$) 345, found 345.

Example 6

This example illustrates the preparation of N-(2-(2-(4-tert-butylphenyl)-5-methoxy-1H-indol-3-yl)ethyl)acetamide. N-(2-(2-bromo-5-methoxy-1H-indol-3-yl)ethyl)acetamide (280 mg, 0.90 mmol) was dissolved in a mixture of toluene (11 mL) and ethanol (11 mL). 4-t-butylphenylboronic acid (186 mg, 1.35 mmol), LiCl (114 mg, 2.69 mmol) and aqueous sodium carbonate (2.3 mL, 1M) were sequentially added to the solution. Palladium (5 mg) was then added in the presence of an argon atmosphere. The mixture was refluxed for 3.5 hours, and the crude product was purified by flash column chromatography (hexanes:ethyl acetate, 3:2). The final product was a lavender solid (171 mg, 52%). $^1$H NMR (CDCl$_3$, 500 MHz): 8.04 (brs, 1H), 7.50 (s, 4H), 7.28 (d, J=8.8 Hz, 1H), 7.08 (d, J=2.4 Hz, 1H), 6.87 (dd, J=8.7, 2.4 Hz, 1H), 5.48 (brs, 1H), 3.88 (s, 3H), 3.55 (dd, J=12.7, 6.6 Hz, 2H), 3.10 (t, J=6.6 Hz, 2H), 1.76 (s, 3H), 1.36 (s, 9H). ESI-MS: calcd. for C$_{23}$H$_{28}$N$_2$O$_2$Na (M+Na$^+$) 387, found 387.

Example 7

This example illustrates the preparation of N-(2-(2-(3-trifluoromethylphenyl)-5-methoxy-1H-indol-3-yl)ethyl)acetamide. N-(2-(2-bromo-5-methoxy-1H-indol-3-yl)ethyl)acetamide (295 mg, 0.95 mmol) was dissolved in a mixture of toluene (11 mL) and ethanol (11 mL). 3-trifluoromethylphenylboronic acid (271 mg, 1.42 mmol), LiCl (121 mg, 2.85 mmol), and aqueous sodium carbonate (2.4 mL, 1M) were added sequentially. Palladium (5 mg) was then added in the presence of an argon atmosphere. The mixture was refluxed for 5 hours, and the crude product purified by flash column chromatography (hexanes:ethyl acetate, 3:2). The final product was a lavender solid (200 mg, 56%). $^1$H NMR (CDCl$_1$, 500 MHz): 8.15 (brs, 1H), 7.77 (d, J=1.4 Hz, 2H), 7.61-7.59 (m, 3H), 7.30 (d, J=8.8 Hz, 1H), 7.11 (d, J=2.4 Hz, 1H), 6.92 (dd, J=9.0, 2.4 Hz, 1H), 5.55 (brs, 1H), 3.89 (s, 3H), 3.55 (dd, J=13.2, 6.8 Hz, 2H), 3.09 (t, J=7.0 Hz, 2H), 1.82 (s, 3H). ESI-MS: calcd. for C$_{20}$H$_{19}$F$_3$N$_2$O$_2$Na (M+Na$^+$) 399, found 399.

Example 8

This example illustrates the preparation of N-(2-(2-(4-trifluoromethylphenyl)-5-methoxy-1H-indol-3-yl)ethyl)acetamide. N-(2-(2-bromo-5-methoxy-1H-indol-3-yl)ethyl)acetamide (282 mg, 0.91 mmol) was dissolved in a mixture of toluene (12 mL) and ethanol (12 mL). 4-trifluoromethylphenylboronic acid (173 mg, 0.91 mmol), LiCl (116 mg, 2.73 mmol), and aqueous sodium carbonate (2.2 mL, 1M) were added sequentially. Palladium (5 mg) was then added in the presence of an argon atmosphere. The mixture was refluxed for 4 hours, and the crude product was purified by flash column chromatography (hexanes:ethyl acetate, 1:1). The final product was a lavender solid (168 mg, 49%). $^1$H NMR (CDCl$_3$, 500 MHz): 7.44-7.69 (m, 6H), 7.31 (d, J=8.7 Hz, 1H), 7.11 (d, J=2.3 Hz, 1H), 6.92 (dd, J=8.8, 2.4 Hz, 1H), 3.89 (s, 3H), 3.55 (dd, J=11.8, 6.6 Hz, 2H), 3.11 (t, J=7.1 Hz, 2H), 1.84 (s, 3H). ESI-MS: calcd. for C$_{20}$H$_{19}$F$_3$N$_2$O$_2$Na (M+Na$^+$) 399, found 399.

Example 9

This example illustrates the preparation of a pharmaceutical composition comprising an inventive melatonin derivative and albumin. 30 mg N-(2-(2-(4-fluorophenyl)-5-methoxy-1H-indol-3-yl)ethyl)acetamide (as prepared in Example 2) was dissolved in 3.0 mL methylene chloride/methanol (9/1). The solution was added to 27.0 mL of a human serum albumin solution (3% w/v). The mixture was homogenized for 5 minutes at low RPM (Vitris homogenizer, model Tempest I.Q.) to form a crude emulsion, and transferred into a high pressure homogenizer (Avestin). Emulsification was performed at 9000-40,000 psi for at least 5 cycles. The resulting system was transferred into a Rotavap and solvent was rapidly removed at 40° C., at reduced pressure (30 mm Hg), for 20-30 minutes. The resulting dispersion was translucent and the typical average diameter of the resulting particles was in the range 50-220 nm (Z-average, Malvern Zetasizer). The dispersion was further lyophilized for 48 hours. The resulting cake was easily reconstituted to the original dispersion by addition of sterile water or saline. The particle size after reconstitution was the same as before lyophilization. It should be recognized that the amounts, types and proportions of drug, solvents, proteins used in this example are not limiting in anyway.

Example 10

This example illustrates the formation of nanoparticles of the inventive compound by using cavitation and high shear forces during a sonication process. Thus, 20 mg N-(2-(2-(4-fluorophenyl)-5-methoxy-1H-indol-3-yl)ethyl)acetamide (as prepared in Example 2) was dissolved in 1.0 mL methylene chloride. The solution was added to 4.0 mL of a human serum albumin solution (5% w/v). The mixture was homogenized for 5 minutes at low RPM (Vitris homogenizer, model Tempest I.Q.) to form a crude emulsion, and transferred into a 40 kHz sonicator cell. Sonication was performed at 60-90% power at 0° C. for 1 minute (550 Sonic Dismembrator). The mixture was transferred into a Rotary evaporator, and methylene chloride was rapidly removed at 40° C., at reduced pressure (30 mm Hg), for 20-30 minutes. The diameter of the resulting particles was 300-420 nm (Z-average, Malvern Zetasizer).

The dispersion was further lyophilized for 48 h without adding a cryoprotectant. The resulting cake was easily reconstituted to the original dispersion by addition of sterile water or saline. The particle size after reconstitution was the same as before lyophilization.

Example 11

This example illustrates the determination of the binding constant ($K_D$) of melatonin and its analogs for $GABA_A$ Cl channel, and binding constant was determined as the following: frozen bovine hippocampus was thawed and homogenized in 40 volumes of ice-cold 0.32 M sucrose. The suspension was centrifuged at 1000×g for 10 minutes at 4° C. The pellet was washed twice in assay buffer and reacted with radioactive ligand in presence or absence of propofol at $10^{-4}$ M final concentration. The amount of radioactivity remained on the Whatman filter following filtration of the reaction mix and two washes with assay buffer was determined using a liquid scintillation counter. Inhibition of radioactive ligand binding by melatonin represents the competitive binding of melatonin to the same site as the radioactive ligand. $GABA_A$ Cl channel were assayed using $^3$H-TBOB. The binding was carried out in the presence of increasing concentration of melatonin and the $K_D$ determined graphically using the Hill plots. The data are shown in Table 2. In vivo hypnotic activity was determined as follow. Drugs solubilized in DMSO were administered to rats by tail vein injection (N=5 rats per group). A dose level of 28 μmol/kg (5 mg/kg for propofol) was used to compensate for differences in molecular weight of the analogs. Anesthetic activity in vivo was determined as time to recovery of righting reflex following administration of the compounds.

TABLE 2

Activity of propofol and melatonin analogs in vitro and in vivo.

| Chemical structure | Anesthesia Activity (Time to awakening, min) | $GABA_A$ Cl Channel Binding ($IC_{50}$, μM) |
|---|---|---|
| 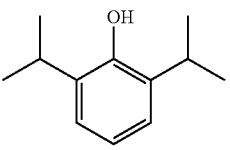 | 20.8 | 4.86 |
| 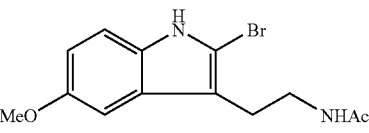 | nd | nd |
| 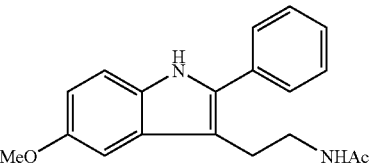 | 2.5 | 108 |

TABLE 2-continued

Activity of propofol and melatonin analogs in vitro and in vivo.

| Chemical structure | Anesthesia Activity (Time to awakening, min) | GABA$_A$ Cl Channel Binding (IC$_{50}$, µM) |
|---|---|---|
| 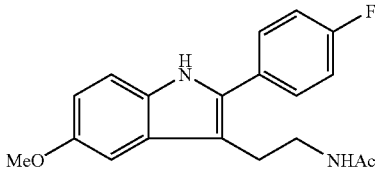 | 3.0 | 27.9 |
| 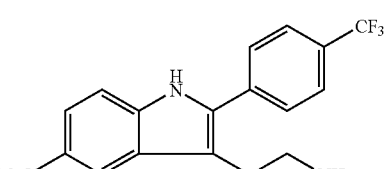 | 20.8 | 13.1 |
| 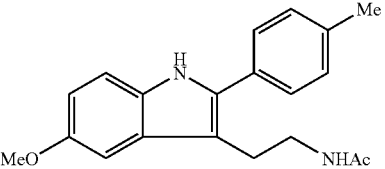 | 4.8 | 33.9 |
| 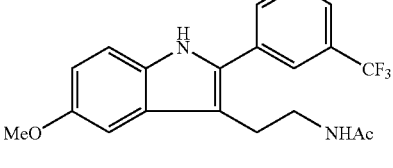 | 3.8 | nd |
| 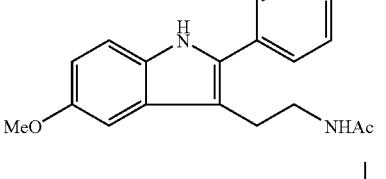 | 3.5 | 19.9 |
| 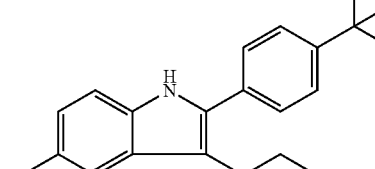 | 20.3 | nd | nd: not done

Example 12

This example demonstrated the preparation of melatonin-albumin compositions for intravenous delivery. 75 mg of melatonin was dissolved in 1.1 mL of ethanol and the ethanol solution is then added into 13.8 mL of human serum albumin (5% w/v). The mixture was homogenized for 5 minutes at low RPM (Virtis homogenizer model: Tempest I.Q.) in order to form a crude emulsion, and then transferred into a high pressure homogenizer (Avestin). The emulsification was performed between 9,000 and 30,000 psi and recycling the emulsion for at least 3 cycles. The resulting system was transferred into a rotary evaporator and the solvent was removed at 35-45° C. at reduced pressure for 3-15 minutes. The resulting particle dispersion was in the range of 15-100 nm (z-average, Malvern Zetasizer). This suspension was sterile filtered with 0.22 µm filter and lyophilized to produce a dry powder cake, which was easily reconstituted with Water for Irrigation or Saline with no observed particle size change.

As shown in Example 12, the composition with the following components can be prepared.

|  | Quantity |
|---|---|
| Melatonin | 0.1-1% (w/v) |
| Ethanol | 0-30% (v/v) |
| Albumin, Human Serum | 1-20% (w/v) |
| Water for irrigation | 70-96% (v/v) |

Example 13

This example demonstrated the preparation of melatonin-albumin nanoparticle with surfactants for intravenous delivery. Nanoparticles of melatonin were produced by high pressure homogenization of melatonin dispersed into a surfactant, and prepared as the Example 1. The surfactant can be in 0.01-1% (w/v). The examples are: PEG 400, PEG 300, Tween 80, lecithins, and Cremophor EL.

Example 14

This example demonstrated the preparation of melatonin-albumin nanoparticle with other solvents for intravenous delivery. Nanoparticles of melatonin were produced by high pressure homogenization of melatonin dissolved in a solvent as described in Example 1. The solvent can be in the range of 0.1-20% (v/v). The examples are: ethanol, methanol, isopropyl alcohol, chloroform, methylene chloride, dimethylacetamide, N-methylpyrrolidone, dimethylisosorbide, ethyl acetate, butyl acetate, benzyl alcohol, and dimethyl sulfoxide.

Example 15

This example demonstrated the preparation of melatonin-albumin nanoparticle with other excipients for intravenous delivery. Nanoparticles of melatonin were produced by high pressure homogenization of melatonin dissolved in a solvent described in Example 1. The other excipients can be in 1-20% (w/v). The examples are mannitol, sucrose, trehalose and dextran or their combinations.

Example 16

This example demonstrated the preparation of melatonin-albumin compositions with PEG 400 for intravenous delivery. The formulation was prepared as described in experiment 1. Prior to filtration, 750 µl of PEG 400 was added and mixed well on a magnetic stir plate. The final size was between 15-100 nm (Z-average, Malvern Zetasizer) The mixture was filtered through 0.22 µm filter and lyophilized. The resulting dry powder was reconstituted with either Water for Irrigation or saline. This dry powder formulation is stable for at least one month at 40° C.

Example 17

This example demonstrated the preparation of melatonin-albumin compositions with mannitol and sucrose for intravenous delivery. The formulation with the following components was prepared as described in experiment 1. Prior to filtration, 1.9 mL of 20% mannitol:sucrose (4:1) was added to the suspension. The final size was between 15-100 nm (Z-average, Malvern Zetasizer). This solution was then sterile filtered, dispensed into bottles and lyophilized. The resulting dry powder was reconstituted with either water for irrigation or saline with nanoparticles in the range of 15-150 nm. The protein nanoparticles are stable at an accelerated condition of 40° C. and 75% relative humidity.

Example 18

This example demonstrated the preparation of melatonin-PEG 400 compositions with the following components:

|  | Quantity |
|---|---|
| Melatonin | 1-40% (w/v) |
| PEG 400 | 0-100% (v/v) |
| Additional solvent | 0-100% (v/v) |

Melatonin was dissolved in an injectable solvent or a combination of injectable solvents at 0-100° C. Possible injectable solvents used in the formulation include but are not limited to ethanol, dimethylacetamide, N-methylpyrrilidinone, glycerin, and propylene glycol.

For example, 750 mg of Melatonin was dissolved in 5 mL of PEG 400 by gently heating to 40-100° C. This solution was either sterile filtered or autoclaved. This solution is stable under an accelerated condition of 40° C. and 75% relative humidity. In preparation for delivery, the solution maybe Diluted with either Water for Irrigation or saline in a range of 1-10 mg/mL; this preparation is stable for more than 3 days.

Example 19

This example demonstrated the preparation of melatonin-PEG 400-solvent compositions for intravenous delivery. 750 mg of melatonin was dissolved in 2.5 mL of PEG 400 by gently heating to 40-100° C. To this solution, 2.5 mL of dimethylacetamide was added. The resultant clear liquid was either sterile filtered or autoclaved. The mixture was stable at 40° C. monitored with HPLC. For administration this solution maybe diluted with either Water for Irrigation or saline in a range of 1-10 mg/mL.

Example 20

This example illustrates the tail clamping with melatonin analogs. Dawley rats (Harlan, Indianapolis, Ind., USA) were weighed and anaesthetized with isoflurane. In all rats, the right jugular vein was cannulated with a heparinized saline filled catheter. Studies were carried out 5-7 days after surgery.

Then the different groups of rats were assigned to receive a single i.v. bolus of the compounds in this invention (dissolved in 10% ethanol/16% Cremophor) and response to tail clamping was assessed. Tail clamp was tested by application of a rubber-clad vascular clamp (22 cm DeBakey) across the proximal third of the tail. Purposeful movement of the hind limbs and/or the head was noted as a positive response. Table 1 summarized the time of lack of response to tail clamping after bolus injection of melatonin and its analogs.

TABLE 1

Lack of response to the tail clamp on rats.

| Compounds Structure | Dose, mg/kg | Time of lack of response to the tail clamp, min | # lack of response rat/tested rat |
|---|---|---|---|
| MeO-indole-2-phenyl-3-CH2CH2NHAc | 15 | No effect | 0/5 |
| MeO-indole-2-(4-F-phenyl)-3-CH2CH2NHAc | 15 | 2 | 5/5 |
| MeO-indole-2-(4-CF3-phenyl)-3-CH2CH2NHAc | 15 | 15 | 4/5 |
| MeO-indole-2-(3-CF3-phenyl)-3-CH2CH2NHAc | 15 | 5 | 5/5 |
| MeO-indole-2-(4-tBu-phenyl)-3-CH2CH2NHAc | 15 | 5 | 5/5 |

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of the formula

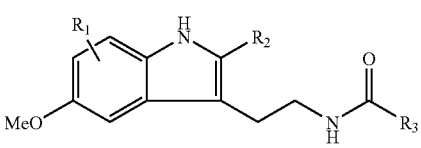

wherein
R$_1$ is a halogen or nitro,
R$_2$ is C$_4$-C$_{20}$ aryl,
R$_3$ is methoxy, ethoxy, amino or dimethylamino.

2. The compound of claim 1, wherein R$_3$ is methoxy.
3. The compound of claim 1, wherein R$_3$ is ethoxy.
4. The compound of claim 1, wherein R$_3$ is amino.
5. The compound of claim 1, wherein R$_3$ is dimethylamino.
6. The compound of claim 1, wherein R$_2$ is selected from the group consisting of phenyl, 4-(fluorophenyl), 3-(fluorophenyl), 2-(fluorophenyl), 4-(chlorophenyl), 3-(chlorophenyl), 2-(chlorophenyl), 4-(methylphenyl), 3-(methylphenyl), 2-(methylphenyl), 4-(methoxyphenyl), 3-(methoxyphenyl), 2-(methoxyphenyl), 4-(ethoxyphenyl), 3-(ethoxyphenyl), 2-(ethoxyphenyl), 4-(vinylphenyl), 4-(acetylphenyl), 3-(acetylphenyl), 2-(acetylphenyl), 4-(trifluoromethylphenyl), 3-(trifluoromethylphenyl), 4-(trimethylsilylphenyl), 3-(trimethylsilylphenyl), 4-(methylthiophenyl), 4-(tert-butylphenyl), 4-(dimethylaminophenyl), 4-(ethylphenyl), 4-(benzoxyphenyl), 4-(biphenyl), 2-furanyl, 2-(thiophenyl), 2-(5-methylthiophenyl), 3-(thiophenyl), 2-(indolyl), 1-(naphthalenyl), 2-(naphthalenyl), 4-(dibenzofuranyl), 1-(thianthrenyl), 2,3-(dichlorophenyl), 2,5-(dichlorophenyl), 3,4-(dichlorophenyl), 3,5-(dichlorophenyl), 2,3-(difluorophenyl), 2,4-(difluorophenyl), 2,5-(difluorophenyl), 2,6-(difluorophenyl), 3,4-(difluorophenyl), 3,5-(difluorophenyl), 3,5-(dibromophenyl), 3,5-(bis(trifluoromethyl)phenyl), 2,3-(dimethylphenyl), 2,5-(dimethylphenyl), 2,6-(dimethylphenyl), 3,5-(dimethylphenyl), 2,4-(dimethoxyphenyl), 2,5-(dimethoxyphenyl), 3,4-(dimethoxyphenyl), 2,3,4-(trimethoxyphenyl), 2,4,6-(trifluorophenyl), and 2,3,4,5,6-(pentafluorophenyl).

7. The compound of claim 1, wherein the compound is N-(2-(5-methoxy-2-methoxyphenyl-1H-indol-3-yl)ethyl) acetamide.

8. The compound of claim 1, wherein the compound is N-(2-(5-methoxy-2-p-tolyl-1H-indol-3-yl)ethyl)acetamide.

9. The compound of claim 1, wherein the compound is N-(2-(2-(4-tert-butylphenyl)-5-methoxy-1H-indol-3-yl) ethyl)acetamide.

10. The compound of claim 1, wherein the compound is N-(2-(2-(3-trifluoromethylphenyl)-5-methoxy-1H-indol-3-yl)ethyl)acetamide.

11. The compound of claim 1, wherein the compound is N-(2-(2-(4-trifluoromethylphenyl)-5-methoxy-1H-indol-3-yl)ethyl)acetamide.

12. A pharmaceutical composition comprising a therapeutically effective amount of the compound of claim 1 and a pharmaceutically acceptable carrier or diluent.

13. A pharmaceutical composition comprising a therapeutically effective amount of the compound of claim 6 and a pharmaceutically acceptable carrier or diluent.

14. A pharmaceutical composition comprising a therapeutically effective amount of nanoparticles of the compound of claim 1 and a pharmaceutically acceptable carrier.

15. A pharmaceutical composition comprising a therapeutically effective amount of nanoparticles of the compound of claim 6 and a pharmaceutically acceptable carrier.

16. A pharmaceutical composition comprising an anesthetic inducing effective amount of the compound of claim 1 and a pharmaceutically acceptable anesthetic carrier.

17. A pharmaceutical composition comprising an anesthetic inducing effective amount of the compound of claim 6 and a pharmaceutically acceptable anesthetic carrier.

18. The compound of claim 1, wherein $R_2$ is a substituted $C_4$-$C_{20}$ aryl.

19. The compound of claim 18, wherein the substituted $C_4$-$C_{20}$ aryl is substituted by one or more of halogen, $C_1$-$C_6$ alkoxy, amino, alkylamino, thiol, alkythiol, hydroxyl, —CHO, —NO$_2$, phenyl, vinyl, —CN, Si(CH$_3$)$_3$, —OCH$_2$O—, or combinations thereof.

20. The compound of claim 6, wherein $R_2$ is a substituted $C_4$-$C_{20}$ aryl.

21. The compound of claim 20, wherein the substituted $C_4$-$C_{20}$ aryl is substituted by one of more of halogen, $C_1$-$C_6$ alkoxy, amino, alkylamino, thiol, alkythiol, hydroxyl, —CHO, —NO$_2$, phenyl, vinyl, —CN, Si(CH$_3$)$_3$, —OCH$_2$O—, or combinations thereof.

22. The compound of claim 2, wherein $R_2$ is selected from the group consisting of phenyl, 4-(fluorophenyl), 3-(fluorophenyl), 2-(fluorophenyl), 4-(chlorophenyl), 3-(chlorophenyl), 2-(chlorophenyl), 4-(methylphenyl), 3-(methylphenyl), 2-(methylphenyl), 4-(methoxyphenyl), 3-(methoxyphenyl), 2-(methoxyphenyl), 4-(ethoxyphenyl), 3-(ethoxyphenyl), 2-(ethoxyphenyl), 4-(vinylphenyl), 4-(acetylphenyl), 3-(acetylphenyl), 2-(acetylphenyl), 4-(trifluoromethylphenyl), 3-(trifluoromethylphenyl), 4-(trimethylsilylphenyl), 3-(trimethylsilylphenyl), 4-(methylthiophenyl), 4-(tert-butylphenyl), 4-(dimethylaminophenyl), 4-(ethylphenyl), 4-(benzoxyphenyl), 4-(biphenyl), 2-furanyl, 2-(thiophenyl), 2-(5-methylthiophenyl), 3-(thiophenyl), 2-(indolyl), 1-(naphthalenyl), 2-(naphthalenyl), 4-(dibenzofuranyl), 1-(thianthrenyl), 2,3-(dichlorophenyl), 2,5-(dichlorophenyl), 3,4-(dichlorophenyl), 3,5-(dichlorophenyl), 2,3-(difluorophenyl), 2,4-(difluorophenyl), 2,5-(difluorophenyl), 2,6-(difluorophenyl), 3,4-(difluorophenyl), 3,5-(difluorophenyl), 3,5-(dibromophenyl), 3,5-(bis(trifluoromethyl)phenyl), 2,3-(dimethylphenyl), 2,5-(dimethylphenyl), 2,6-(dimethylphenyl), 3,5-(dimethylphenyl), 2,4-(dimethoxyphenyl), 2,5-(dimethoxyphenyl), 3,4-(dimethoxyphenyl), 2,3,4-(trimethoxyphenyl), 2,4,6-(trifluorophenyl), and 2,3,4,5,6-(pentafluorophenyl).

23. The compound of claim 3, wherein $R_2$ is selected from the group consisting of phenyl, 4-(fluorophenyl), 3-(fluorophenyl), 2-(fluorophenyl), 4-(chlorophenyl), 3-(chlorophenyl), 2-(chlorophenyl), 4-(methylphenyl), 3-(methylphenyl), 2-(methylphenyl), 4-(methoxyphenyl), 3-(methoxyphenyl), 2-(methoxyphenyl), 4-(ethoxyphenyl), 3-(ethoxyphenyl), 2-(ethoxyphenyl), 4-(vinylphenyl), 4-(acetylphenyl), 3-(acetylphenyl), 2-(acetylphenyl), 4-(trifluoromethylphenyl), 3-(trifluoromethylphenyl), 4-(trimethylsilylphenyl), 3-(trimethylsilylphenyl), 4-(methylthiophenyl), 4-(tert-butylphenyl), 4-(dimethylaminophenyl), 4-(ethylphenyl), 4-(benzoxyphenyl), 4-(biphenyl), 2-furanyl, 2-(thiophenyl), 2-(5-methylthiophenyl), 3-(thiophenyl), 2-(indolyl), 1-(naphthalenyl), 2-(naphthalenyl), 4-(dibenzofuranyl), 1-(thianthrenyl), 2,3-(dichlorophenyl), 2,5-(dichlorophenyl), 3,4-(dichlorophenyl), 3,5-(dichlorophenyl), 2,3-(difluorophenyl), 2,4-(difluorophenyl), 2,5-(difluorophenyl), 2,6-(difluorophenyl), 3,4-(difluorophenyl), 3,5-(difluorophenyl), 3,5-(dibromophenyl), 3,5-(bis(trifluoromethyl)phenyl), 2,3-(dimethylphenyl), 2,5-(dimethylphenyl), 2,6-(dimethylphenyl), 3,5-(dimethylphenyl), 2,4-(dimethoxyphenyl), 2,5-(dimethoxyphenyl), 3,4-(dimethoxyphenyl), 2,3,4-(trimethoxyphenyl), 2,4,6-(trifluorophenyl), and 2,3,4,5,6-(pentafluorophenyl).

24. The compound of claim 4, wherein $R_2$ is selected from the group consisting of phenyl, 4-(fluorophenyl), 3-(fluorophenyl), 2-(fluorophenyl), 4-(chlorophenyl), 3-(chlorophenyl), 2-(chlorophenyl), 4-(methylphenyl), 3-(methylphenyl), 2-(methylphenyl), 4-(methoxyphenyl), 3-(methoxyphenyl), 2-(methoxyphenyl), 4-(ethoxyphenyl), 3-(ethoxyphenyl), 2-(ethoxyphenyl), 4-(vinylphenyl), 4-(acetylphenyl), 3-(acetylphenyl), 2-(acetylphenyl), 4-(trifluoromethylphenyl), 3-(trifluoromethylphenyl), 4-(trimethylsilylphenyl), 3-(trimethylsilylphenyl), 4-(methylthiophenyl), 4-(tert-butylphenyl), 4-(dimethylaminophenyl), 4-(ethylphenyl), 4-(benzoxyphenyl), 4-(biphenyl), 2-furanyl, 2-(thiophenyl), 2-(5-methylthiophenyl), 3-(thiophenyl), 2-(indolyl), 1-(naphthalenyl), 2-(naphthalenyl), 4-(dibenzofuranyl), 1-(thianthrenyl), 2,3-(dichlorophenyl), 2,5-(dichlorophenyl), 3,4-(dichlorophenyl), 3,5-(dichlorophenyl), 2,3-(difluorophenyl), 2,4-(difluorophenyl), 2,5-(difluorophenyl), 2,6-

(difluorophenyl), 3,4-(difluorophenyl), 3,5-(difluorophenyl), 3,5-(dibromophenyl), 3,5-(bis(trifluoromethyl)phenyl), 2,3-(dimethylphenyl), 2,5-(dimethylphenyl), 2,6-(dimethylphenyl), 3,5-(dimethylphenyl), 2,4-(dimethoxyphenyl), 2,5-(dimethoxyphenyl), 3,4-(dimethoxyphenyl), 2,3,4-(trimethoxyphenyl), 2,4,6-(trifluorophenyl), and 2,3,4,5,6-(pentafluorophenyl).

25. The compound of claim 5, wherein $R_2$ is selected from the group consisting of phenyl, 4-(fluorophenyl), 3-(fluorophenyl), 2-(fluorophenyl), 4-(chlorophenyl), 3-(chlorophenyl), 2-(chlorophenyl), 4-(methylphenyl), 3-(methylphenyl), 2-(methylphenyl), 4-(methoxyphenyl), 3-(methoxyphenyl), 2-(methoxyphenyl), 4-(ethoxyphenyl), 3-(ethoxyphenyl), 2-(ethoxyphenyl), 4-(vinylphenyl), 4-(acetylphenyl), 3-(acetylphenyl), 2-(acetylphenyl), 4-(trifluoromethylphenyl), 3-(trifluoromethylphenyl), 4-(trimethylsilylphenyl), 3-(trimethylsilylphenyl), 4-(methylthiophenyl), 4-(tert-butylphenyl), 4-(dimethylaminophenyl), 4-(ethylphenyl), 4-(benzoxyphenyl), 4-(biphenyl), 2-furanyl, 2-(thiophenyl), 2-(5-methylthiophenyl), 3-(thiophenyl), 2-(indolyl), 1-(naphthalenyl), 2-(naphthalenyl), 4-(dibenzofuranyl), 1-(thianthrenyl), 2,3-(dichlorophenyl), 2,5-(dichlorophenyl), 3,4-(dichlorophenyl), 3,5-(dichlorophenyl), 2,3-(difluorophenyl), 2,4-(difluorophenyl), 2,5-(difluorophenyl), 2,6-(difluorophenyl), 3,4-(difluorophenyl), 3,5-(difluorophenyl), 3,5-(dibromophenyl), 3,5-(bis(trifluoromethyl)phenyl), 2,3-(dimethylphenyl), 2,5-(dimethylphenyl), 2,6-(dimethylphenyl), 3,5-(dimethylphenyl), 2,4-(dimethoxyphenyl), 2,5-(dimethoxyphenyl), 3,4-(dimethoxyphenyl), 2,3,4-(trimethoxyphenyl), 2,4,6-(trifluorophenyl), and 2,3,4,5,6-(pentafluorophenyl).

* * * * *